United States Patent [19]

Howard, III et al.

[11] Patent Number: 5,654,803
[45] Date of Patent: Aug. 5, 1997

[54] APPARATUS AND METHOD FOR DETERMINATION OF NON-HEMOLYZED LEVELS OF OCCULT BLOOD IN URINE

[75] Inventors: Willis E. Howard, III, Elkhart; Marilyn Radtke, South Bend; Gary E. Rehm, Elkhart, all of Ind.

[73] Assignee: Bayer Corporation, Elkhart, Ind.

[21] Appl. No.: 647,121

[22] Filed: May 9, 1996

[51] Int. Cl.$^6$ ........................... G01N 21/49
[52] U.S. Cl. ........................... 356/446; 436/169
[58] Field of Search ............ 356/446; 422/82.05; 436/66, 164, 169

[56] References Cited

U.S. PATENT DOCUMENTS

| | | | |
|---|---|---|---|
| 3,907,503 | 9/1975 | Betts et al. | 23/253 |
| 4,755,058 | 7/1988 | Shaffer | 356/408 |
| 5,028,139 | 7/1991 | Kramer et al. | 356/446 |
| 5,165,078 | 11/1992 | Hough et al. | 359/233 |
| 5,246,858 | 9/1993 | Arbuckle et al. | 436/8 |
| 5,250,262 | 10/1993 | Heidt et al. | 422/64 |
| 5,264,348 | 11/1993 | Schick et al. | 435/28 |
| 5,318,984 | 6/1994 | Pugia | 438/28 |
| 5,464,775 | 11/1995 | Smith | 436/63 |

*Primary Examiner*—Frank G. Font
*Assistant Examiner*—Zandra V. Smith
*Attorney, Agent, or Firm*—Roger N. Coe

[57] ABSTRACT

An apparatus for analyzing a body-fluid sample disposed on a reagent pad is provided with a light bulb for successively illuminating a plurality of different portions of the reagent pad on which the body-fluid sample is disposed and a detector array for detecting light received from the reagent pad and generating a plurality of reflectance signals in response to light received from a corresponding one of the different portions of the reagent pad. The apparatus is also provided with means for determining whether the magnitude of one of the reflectance signals is substantially different than the magnitude of another of the reflectance signals. Where the body-fluid sample is urine, this capability allows the apparatus to detect the presence of non-hemolyzed in the urine sample. The light bulb may successively illuminate a plurality of overlapping portions of the reagent pad, and may successively illuminate at least three different portions of the reagent pad which are linearly offset from each other.

22 Claims, 4 Drawing Sheets

APPARATUS AND METHOD FOR DETERMINATION OF NON-HEMOLYZED LEVELS OF OCCULT BLOOD IN URINE

BACKGROUND OF THE INVENTION

The present invention relates to an apparatus and method for performing tests on a sample of body fluid to be analyzed, and more particularly to a reflectance spectroscope and method for determination of non-hemolyzed levels of occult blood in urine.

It is useful for various medical diagnostic purposes to utilize a reflectance spectroscope to analyze samples of body fluid, for example, to detect the presence of blood in a person's urine. Conventional reflectance spectroscopes have been used to detect the presence of blood in a urine sample disposed on a reagent pad. Any blood present in the urine reacts with the reagent on the reagent pad, causing the reagent pad to change color over time to an extent which depends on the concentration of the blood. For example, in the presence of a relatively large concentration of blood, such a reagent pad may change in color from yellow to dark green.

One prior art reflectance spectroscope detects the concentration of the blood by illuminating a single portion of the reagent pad and detecting, via a conventional reflectance detector, the amount of light received from the reagent pad, which is related to the color of the reagent pad. Based upon the magnitude of the reflectance signal generated by the reflectance detector, the spectroscope assigns the urine sample to one of a number of categories, e.g. a first category corresponding to no blood, a second category corresponding to a small blood concentration, a third category corresponding to a medium blood concentration, and a fourth category corresponding to a large blood concentration.

The assignment of a urine sample into one of the categories described above has been performed by successively comparing the magnitude of the reflectance signal with each of three threshold levels which define the categories. For example, if the reflectance signal has a magnitude that corresponds to a 10% light reflectance (which would correspond to a dark reagent pad having a large blood concentration), the spectroscope would compare that 10% reflectance signal with the threshold for large blood concentrations, e.g. 15%, and would assign the urine sample to that category.

One disadvantage of such a conventional spectroscope is the possibility of miscategorizing the blood concentration in cases where non-hemolyzed blood is present. Blood present in a normal urine sample is hemolyzed, which means that the blood is relatively uniformly distributed throughout the urine sample as small blood cell fragments which are visually undetectable. In certain cases, such as in highly concentrated urine, the blood is non-hemolyzed, meaning that there are substantially intact red blood cells or relatively large blood cell fragments present which can be visually detected with the unaided eye or with a small amount of magnification.

When a relatively small amount of non-hemolyzed blood is present in a urine sample, a conventional spectroscope may generate a false negative (erroneously reporting the absence of blood) if the concentration of the individual blood cells is small enough. However, if that same urine sample on the reagent pad were visually inspected by a doctor, the large blood cell fragments could be seen, thus leading the doctor to erroneously believe that the spectroscope was faulty.

SUMMARY OF THE INVENTION

The invention is directed to an apparatus for analyzing a body-fluid sample disposed on a reagent pad. The apparatus is provided with means for successively illuminating a plurality of different portions of the reagent pad on which the body-fluid sample is disposed and means for generating a plurality of reflectance signals in response to light received from a corresponding one of the different portions of the reagent pad illuminated by the illuminating means. The apparatus is also provided with means for determining whether the magnitude of one of the reflectance signals is substantially different than the magnitude of another of the reflectance signals. Where the body-fluid sample is urine, this capability allows the apparatus to detect the presence of non-hemolyzed blood in the urine sample.

The illuminating means may successively illuminate a plurality of overlapping portions of the reagent pad, and may successively illuminate at least three different portions of the reagent pad which are linearly offset from each other. The apparatus may also be provided with means for determining a decode signal based upon the reflectance signals, and means for comparing the decode signal with a plurality of predetermined thresholds to categorize the body-fluid sample.

The apparatus may include means for determining a difference between the magnitude of one of the reflectance signals and the magnitude of another of the reflectance signals and means for comparing the difference with a predetermined threshold to detect the presence of non-hemolyzed blood in the urine sample. The means for determining the difference may include means for determining which of the reflectance signals has the largest magnitude, means for determining which of the reflectance signals has the smallest magnitude, and means for determining a difference between the largest magnitude and the smallest magnitude of the reflectance signals.

The invention is also directed to a method of analyzing a urine sample disposed on a reagent pad. The method includes the steps of: illuminating a first portion of the reagent pad, detecting light received from the first portion of the reagent pad, and generating a first reflectance signal having a magnitude based on the light detected from the first illuminated portion. The method also includes the steps of illuminating a second portion of the reagent pad, detecting light received from the second portion of the reagent pad, and generating a second reflectance signal having a magnitude based on the light detected from the second illuminated portion. The method determines whether the magnitude of the first reflectance signal is substantially different than the magnitude of the second reflectance signal.

In another aspect, the invention is directed to an apparatus for illuminating a body-fluid sample disposed on a reagent pad. The apparatus is provided with means for illuminating a first portion of the reagent pad on which the body-fluid sample is disposed, the first portion of the reagent pad having an area that is smaller than the overall area of the reagent pad. The apparatus includes means for moving the reagent pad relative to the illuminating means so that the illuminating means illuminates a second portion of the reagent pad different from the first portion of the reagent pad, the second portion of the reagent pad having an area that is smaller than the overall area of the reagent pad. The apparatus also includes means for detecting light received from the illuminated portions of the reagent pad.

These and other features and advantages of the present invention will be apparent to those of ordinary skill in the art

DETAILED DESCRIPTION OF A PREFERRED EMBODIMENT

Figure 1:
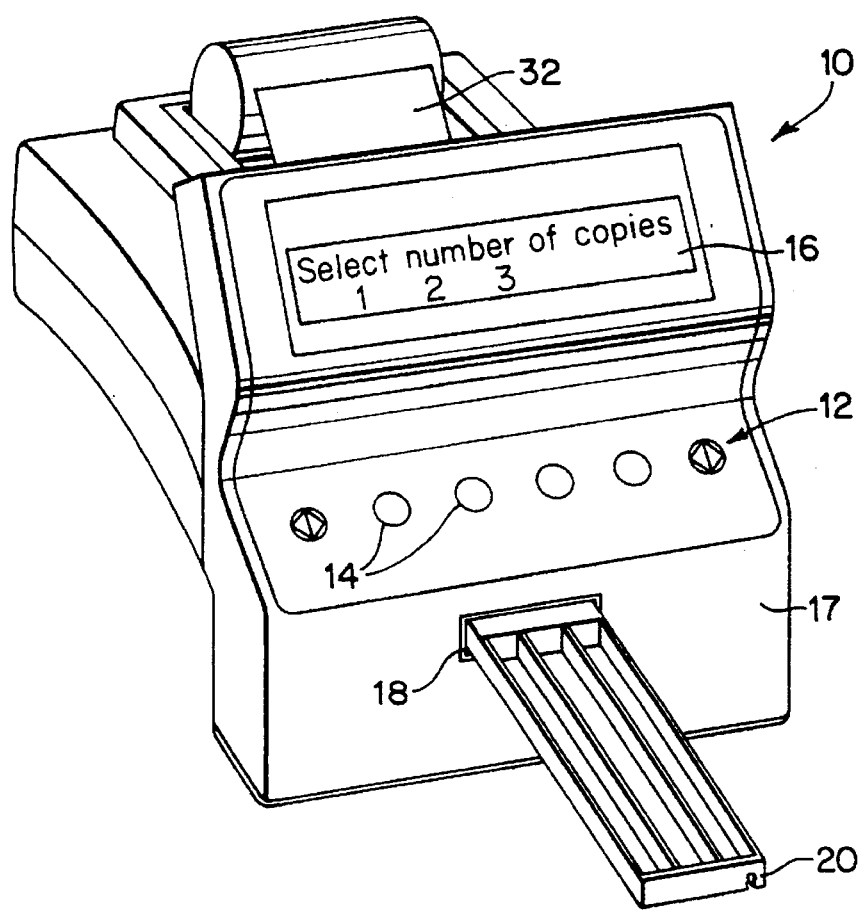
FIG. 1 is a perspective view of a reflectance spectroscope which may be used to perform various tests of a body fluid sample disposed on a reagent strip.
Figure 2:
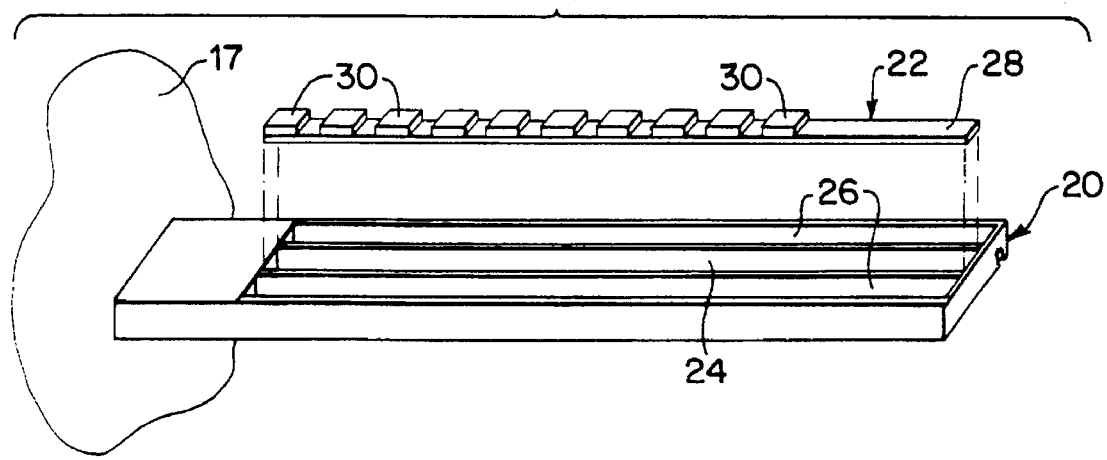
FIG. 2 is a perspective view of a reagent strip and a reagent tray used with the spectroscope of FIG. 1.

FIG. 1 illustrates a reflectance spectroscope 10 for performing various tests, such as urinalysis tests, on a reagent strip. The spectroscope 10 has an integral keyboard 12 with a number of entry keys 14 that may be depressed by the user. A visual display 16 for displaying various messages relating to the operation of the spectroscope 10 is disposed above the keyboard 12. Referring to FIGS. 1 and 2, the spectroscope 10 has a front face 17 with an opening 18 formed therein in which a tray 20 for carrying a reagent strip 22 is retractably disposed. The tray 20 has a central channel 24 and two side channels 26 formed therein, and the central channel 24 is sized to conform to the shape of the reagent strip 22.

The reagent strip 22 has a thin, non-reactive substrate 28 on which a number of reagent pads 30 are fixed. Each reagent pad 30 is composed of a relatively absorbent material impregnated with a respective reagent, each reagent and reagent pad 30 being associated with a particular test to be performed. When urinalysis tests are performed, they may include, for example, a test for leukocytes in the urine, a test of the pH of the urine, a test for blood in the urine, etc. When each reagent pad 30 comes into contact with a urine sample, the pad changes color over a time period, depending on the reagent used and the characteristics of the urine sample. The reagent strip 22 may be, for example, a Multistix® reagent strip commercially available from Bayer Corporation.

To perform urinalysis testing, the reagent strip 22 is dipped into a urine sample to be tested so that all of the reagent pads 30 are immersed in the sample. After the side of the reagent strip 22 is blotted to remove excess urine, the strip 22 is placed in the central channel 24 of the tray 20, and after the user presses one of the start keys 14 to initiate testing, the tray 20 is automatically retracted into the spectroscope 10.

A respective test is performed on each of the reagent pads 30 by illuminating a portion of the reagent pad 30 with white light from a light source and then determining the color of the reagent pad 30 based upon detection of light received from the illuminated portion of the reagent pad 30 at an angle (e.g. 45°) from the upper surface of the pad 30. After each test is performed, the tray 20 is repositioned relative to the light source so that the next reagent pad 30 to be tested is illuminated. When the testing is completed, the spectroscope 10 generates a record of the results, which are displayed on the display 16 and/or printed on a strip of paper 32 via a printer and/or sent to a computer.

Read Head

Figure 3:
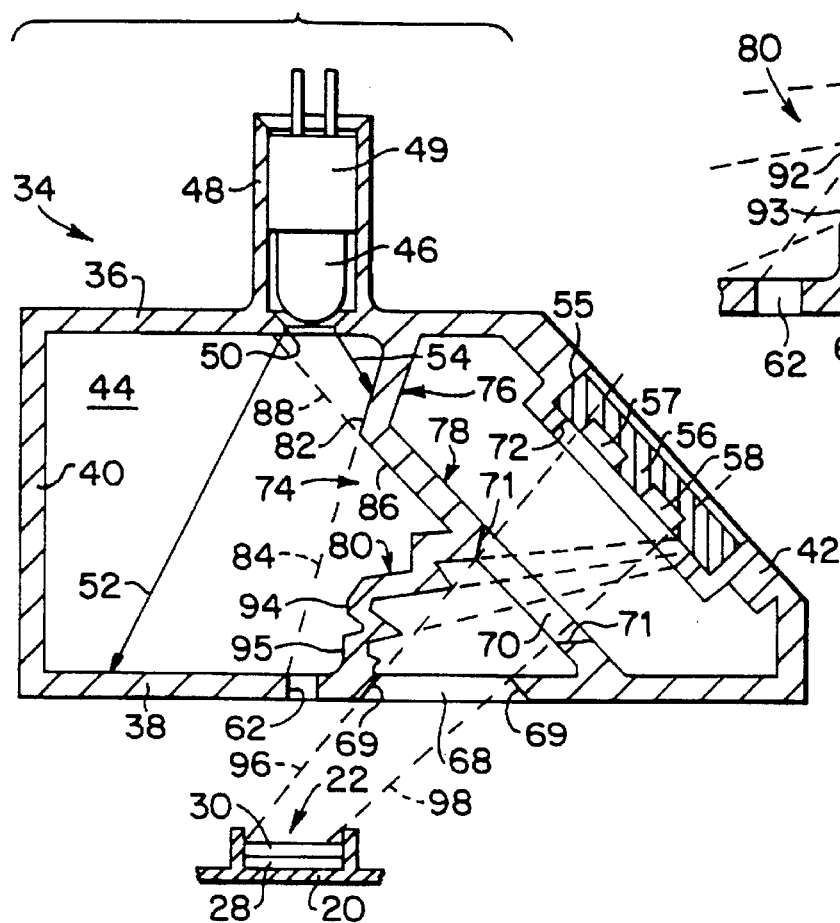
FIG. 3 is a cross-sectional view of a read head used in the spectroscope.

FIG. 3 is a cross-sectional view of an optical system, in the form of a read head 34, for illuminating portions of the reagent pads 30 and for detecting light from the reagent pads 30, and a portion of the tray 20 on which the reagent strip 22 is disposed. Referring to FIG. 3, the read head 34 has a housing with a top wall 36, a bottom wall 38, a side wall 40, an angled wall 42, a planar back wall 44, and a planar front wall (not shown) parallel to the back wall 44. An illumination source in the form of a light bulb 46 is supported directly above the reagent pad 30 to be tested via a cylindrical housing portion 48 integrally formed with the top wall 36.

The lower spherical portion of the light bulb 46 has a concentrating lens integrally formed therein, and the lower spherical surface is acid-etched to provide it with an uneven, diffusing surface so that the shape of the bulb filament does not contribute to non-uniformity of the emitted light. When manufactured, the bulb 46 is dynamically fitted to a ceramic base 49 when the bulb 46 is illuminated to ensure that the axial direction in which bulb 46 emits light is substantially parallel to the longitudinal axis of the ceramic base 49. The bulb 46 emits light through a circular aperture 50 formed in the top wall 36 to form a cone of light defined by a first edge ray 52 and a second edge ray 54.

Figure 4:
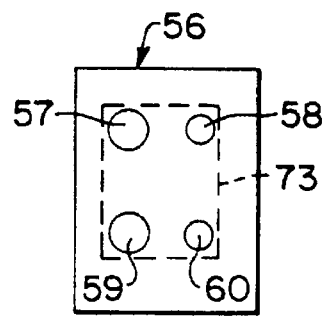
FIG. 4 is a schematic view of a detector element used in the spectroscope.

The angled side wall 42 has a rectangular aperture 55 formed therein in which a rectangular detector array 56 is disposed. The detector array 56 has four reflectance detectors 57, 58, 59, 60 disposed therein (see FIG. 4), each of which is composed of a conventional colored or IR filter and a conventional silicon detector. Each filter allows light having a distinct wavelength to pass through so that each of the detectors 57–60 is responsive to light of a different wavelength range. The four wavelength bands of the filters are: 400–510 nm (nanometers) (blue); 511–586 nm (green); 587–660 nm (red); and 825–855 nm (infrared). Depending on the type of test being performed, one or more of the detectors 57–60 may be used.

Light passes through a first optical path from the light bulb 46, through a relatively small rectangular aperture 62 formed in the bottom wall 38, to illuminate a relatively small rectangular area of the reagent pad 30 being tested. The reagent pad 30 may be moved relative to the aperture 62 so that different rectangular areas of the reagent pad 30 are illuminated.

Figure 5:
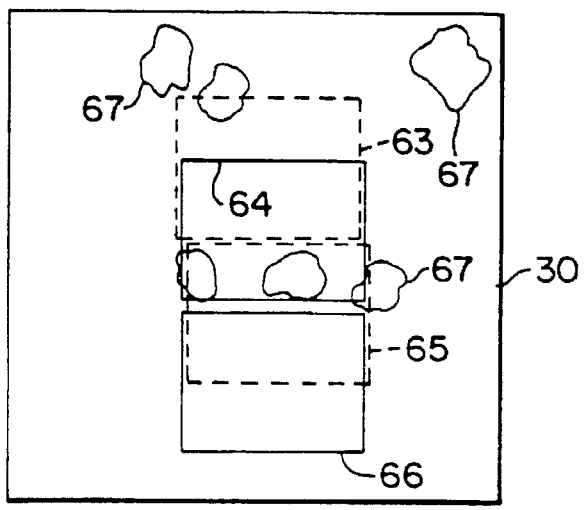
FIG. 5 is an enlarged view of a reagent pad and a number of illuminated areas on the reagent pad.

Referring to FIG. 5, the illuminated areas may include a first area indicated by a dotted box 63, a second area indicated by a solid box 64, a third area indicated by a dotted box 65, and a fourth area indicated by a solid box 66. Although shown slightly vertically offset in FIG. 5 so that each box can be distinctly seen, the illuminated areas 63–66 are linearly offset with respect to each other, and adjacent areas partially overlap each other. A number of irregularly shaped areas 67 representing non-hemolyzed blood cell fragments are also shown in FIG. 5.

Light passes through a second optical path from the illuminated area on the reagent pad 30, through a first rectangular detection aperture 68 having angled edges 69 formed in the bottom wall 38, through a second rectangular detection aperture 70 having angled edges 71, and through a rectangular aperture 72 formed in the angled wall 42 to a detection area 73 (FIG. 4) in which the four detectors 57–60 are disposed.

The interior of the read head 34 is provided with an irregularly shaped baffle 74 composed of a first planar wall segment 76, a second planar wall segment 78, and a zig-zag shaped wall segment 80. The shape of the baffle 74 is designed to prevent singly-reflected light rays from reaching the reagent pad 30 from the light bulb 46 and to prevent singly-reflected light rays from reaching the detector area 73 from the reagent pad 30.

All surfaces of the baffle 74 and all interior surfaces of the housing walls 36, 38, 40, 42, 44 are shiny, specular surfaces so that any light incident upon any surface at an angle of incidence is reflected from that surface at an angle of reflection equal to the angle of incidence. This may be accomplished by injection-molding the read head 34 from a metal mold having highly polished molding surfaces. The read head 34 is preferably formed of black plastic so that only a small percentage of light, e.g. 5%, incident upon any of its internal surfaces is reflected. Consequently, any light that undergoes at least two reflections from any interior surfaces of the read head 34 is attenuated by at least 99.75%.

Referring to FIG. 3, the wall segment 76 has a specular surface 82 that is angled in a direction indicated by a dotted line 84, which intersects the bottom wall 38 at a point just to the left of the aperture 62. Consequently, any light rays emitted by the bulb 46 that impinge upon the surface 82 are reflected to an area to the left of the aperture 62. It should be noted that any such rays are reflected at least twice (in actuality at least three times) before they can pass through the aperture 62. It should also be noted that no light can be reflected from the surface 82 and pass directly through the aperture 62 without further reflection since the surface 82 is not visible when the interior of the read head 34 is viewed from the aperture 62.

The wall segment 78 has a specular surface 86 angled in a direction indicated by a dotted line 88, which intersects the top wall 36 at a point to the left of the circular opening 50 through which light passes. Consequently, there is no direct path from the light bulb 46 to the surface 86; therefore, any light that is reflected from the surface 86 to the aperture 62 will have undergone at least two (more than two in actuality) reflections from the interior surfaces of the read head 34.

Figure 3A:
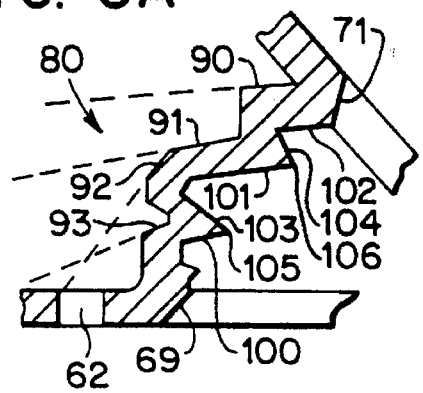
FIG. 3A is an enlarged view of a portion of the read head shown in FIG. 3.

FIG. 3A is an enlarged view of a portion of read head 34 shown in FIG. 3. Referring to FIGS. 3 and 3A, the zig-zag wall segment 80 has angled surfaces 90–93, each of which is angled in a direction indicated by a respective dotted line. Since all of the dotted lines intersect the bottom wall 38 or the side wall 40 to the left of the aperture 62, no light that impinges upon these surfaces 90–93 directly from the light bulb 46 can be reflected directly to the aperture 62. The zig-zag wall segment 80 has two further surfaces 94, 95 (FIG. 3) that are angled so that any light that impinges on those surfaces directly from the bulb 46 is reflected exclusively to the area of the bottom wall 38 to the right side of the aperture 62.

The only surfaces from which light rays emitted by the bulb 46 can be singly-reflected and still pass through the aperture 62 are the vertical walls of the aperture 62 itself. However, such singly-reflected light rays constitute an insignificant amount of the total light which passes directly from the light bulb 46 to the reagent pad 30 without reflection. There is also a singly-reflected light path from the bulb 46 to the walls 40 or 44 to the aperture 62. But because the bulb 46 concentrates light in a forward direction within the cone defined by rays 52 and 54, the amount of light going through the aperture 62 from this path is insignificant.

The second optical path, from the reagent pad 30 to the detector area 73 (FIG. 4), is generally indicated by a pair of dotted lines 96, 98. The side of the zig-zag wall segment 80 which is disposed adjacent the second optical path has a plurality of planar, specular surfaces 100, 101, 102 which are angled in a direction indicated by a number of corresponding dotted lines (shown in FIG. 3) which intersect the angled side wall 42 at a point to the lower right of the detector area 73. Consequently, any light rays that impinge upon these surfaces 100–102 directly from the reagent pad 30 without reflection cannot reach the detector area 73 without at least one more reflection, and thus any such light rays will be attenuated by at least 99.75%.

The side of the zig-zag wall segment 80 which is disposed adjacent the second optical path has a plurality of planar, specular surfaces 103, 104 (FIG. 3A) which are angled so that no light rays from the reagent pad 30 can reach the surfaces 103, 104 directly without at least one reflection. Consequently, any light rays that impinge upon these surfaces 103–104 will already have undergone at least one reflection, and therefore any such light rays that eventually reach the detector area 73 will be reflected at least twice and thus be attenuated by at least 99.75%.

The wall surfaces 100 and 103 join at an edge 105, and the wall surfaces 101 and 104 join at an edge 106, the edges 105, 106 being substantially aligned with a respective edge of the detection area 73, and the edges 69, 71 of the detection apertures 68, 70 are aligned with the edges of the detection area 73.

Electronics

Figure 6:
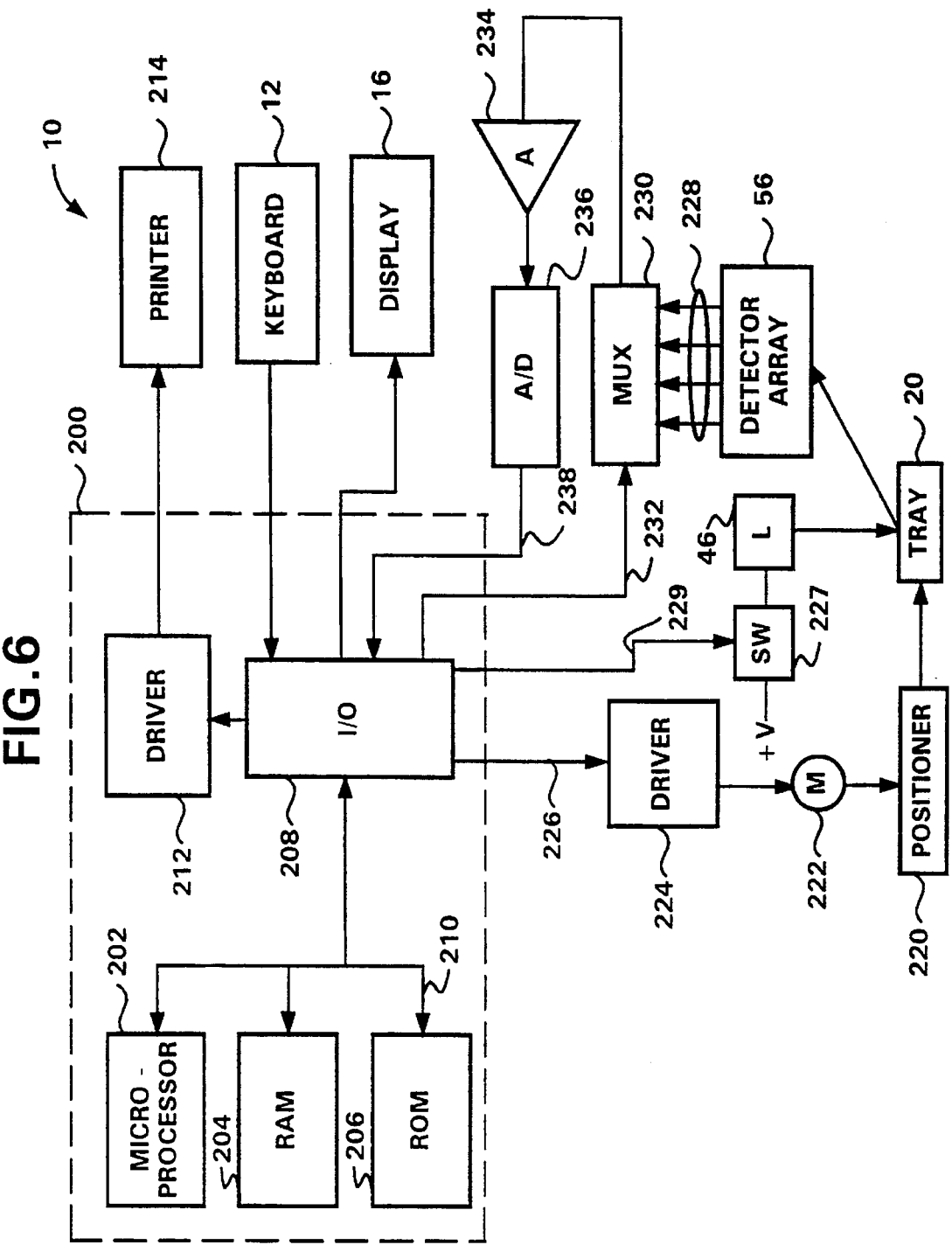
FIG. 6 is a block diagram of the electronics of the spectroscope of FIG. 1.

FIG. 6 is a block diagram of the electronics and other components of the spectroscope 10. Referring to FIG. 6, the operation of the spectroscope 10 is controlled by a microcontroller 200 which has a microprocessor 202, a random-access memory (RAM) 204, a read-only memory (ROM) 206, and an input/output (I/O) circuit 208, all of which are interconnected via an address/data bus 210. The microcontroller 200, which may be a conventional microcontroller such as a DS2253T microcontroller commercially available from Vallas Semiconductor, may incorporate a driver circuit 212 connected to the I/O circuit 208 for driving a printer 214.

The microcontroller 200 controls the movement of the reagent strip tray 20 via a conventional positioner 220 mechanically coupled to the tray 20 and a motor 222, such as a stepping motor, that is driven by drive signals generated by a driver circuit 224 connected to the I/O circuit 208 via an electrical line 226.

The microcontroller 200 selectively turns on the light bulb 46 via a switch 227 connected to the I/O circuit 208 via an electrical line 229. The light bulb 46 is turned on one second prior to the performance of a test so that it will be sufficiently warmed up. If the light bulb 46 is not needed to provide illumination within the next one-second period following a test, it is turned off to conserve its life.

Each of the detectors 57–60 of the detector array 56 may generate an electrical reflectance signal on one of a number of electrical lines 228. Each reflectance signal has a magnitude that depends on the amount of light detected by the associated detector. The microcontroller 200 can selectively read any one of the reflectance signals by transmitting a select signal to a multiplexer 230 via a line 232. The multiplexer 230 then transmits the selected reflectance signal to an amplifier 234 and an analog-to-digital (A/D) converter 236, which transmits the binary signal corresponding to the analog reflectance signal output by the amplifier 234 to the microcontroller 200 via a line 238 connected to the I/O circuit 208.

Operation

Figure 7:
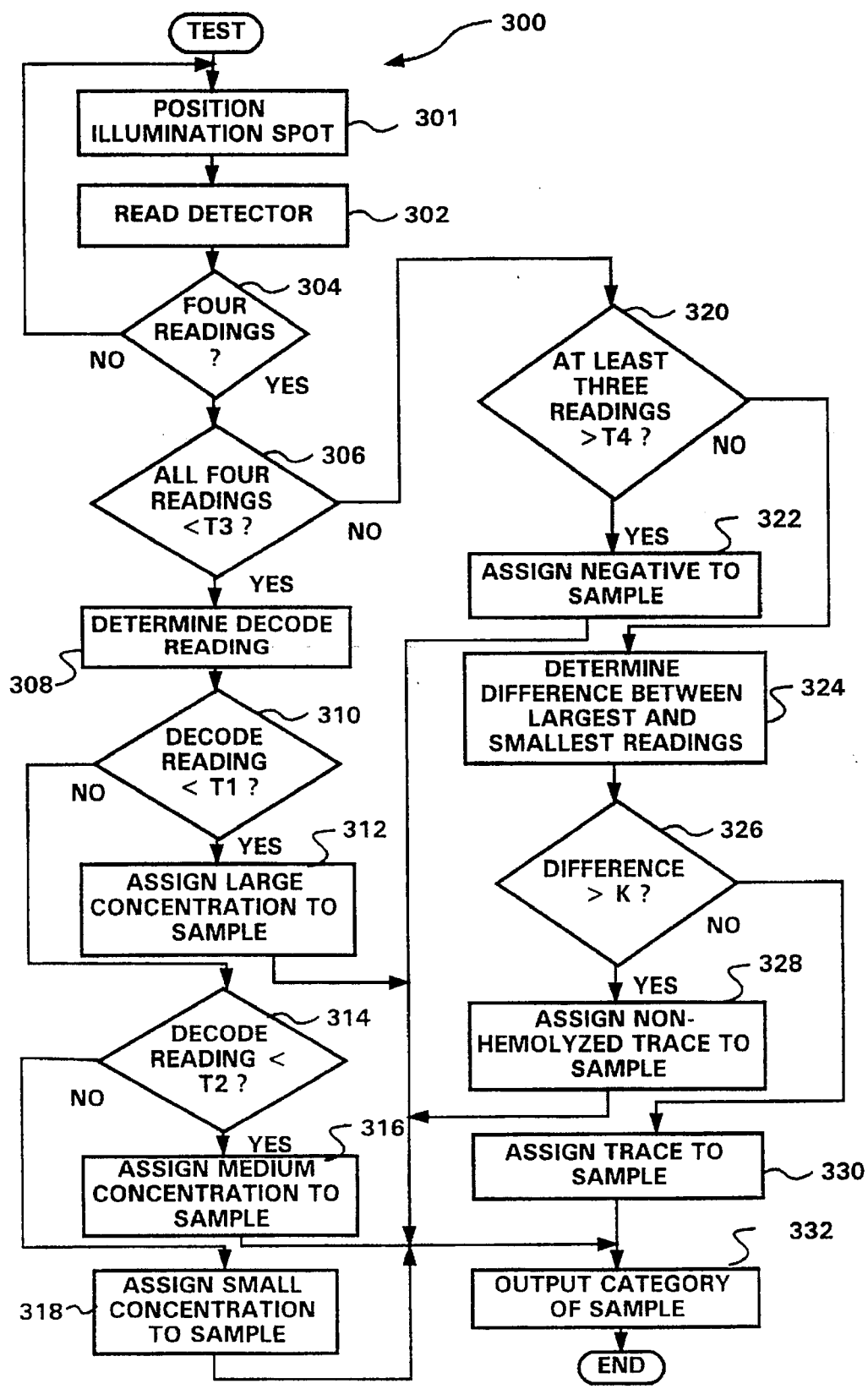
FIG. 7 is a flowchart of a computer program routine that may be used to detect trace levels of non-hemolyzed blood in a urine sample analyzed by the spectroscope.

The operation of the spectroscope 10 is controlled by a computer program stored in the ROM 206 and executed by the microprocessor 202. A flowchart of a test routine 300 which relates to the detection of blood in the urine is shown in FIG. 7. When a urinalysis test is performed, the reagent pad 30 having the reagent which changes color in response to the presence of blood is positioned directly below the light bulb 46. The detector having the red filter is used for urinalysis testing of the reagent pad 30 for the blood test.

The amount of light sensed by the detector from the reagent pad 30 is inversely related to the amount of blood present in the urine sample on the reagent pad. A relatively large blood concentration will cause the reagent pad 30 to turn from yellow to green. Since the color green is darker and absorbs more light than the color yellow, relatively large blood concentrations will cause the red-filter detector to detect a relatively small amount of light.

For each of a plurality of illuminated portions on the reagent pad 30, the red-filter detector generates an electrical reflectance signal having a magnitude directly proportional to the amount of light sensed by the detector from that portion. Based upon the magnitudes of the reflectance signals, the spectroscope 10 associates the urine sample with one of six categories: no blood present, blood trace present, non-hemolyzed blood trace present, a relatively small blood concentration present, a medium blood concentration present, or a relatively large blood concentration present.

The test routine 300 shown in FIG. 7 may be used to perform a single urinalysis test. Referring to FIG. 7, steps 301–304 cause four reflectance readings of the reagent pad 30 to be made, each reading corresponding to a different one of the illuminated portions 63–66 of the reagent pad 30 (FIG. 5). At step 301, the light bulb 46 is turned on to illuminate a first portion of the reagent pad 30, such as the portion 63 shown in FIG. 5. Then at step 302, the reflectance signal generated by the red-filter detector is "read" by transmitting it through the multiplexer 230 to the amplifier 234, the A/D converter 236, the I/O circuit 208, and the RAM 204 where its value is stored. At step 304, if four readings have not been made, the program branches back to step 301 where a different portion of the reagent pad 30 is illuminated, such as the portion 64, and to step 302, where the reflectance reading generated by the detector is read and stored in the RAM 204. Steps 301–302 are repeated until four readings have been taken.

At step 306, if each of the four readings is less than a threshold T3 (e.g. 29.1% reflectance), the program branches to step 308 where a decode reading is determined. The decode reading is used to categorize the urine sample into one of three blood concentration categories: large blood concentration, medium blood concentration, or small blood concentration. At step 308, the decode reading may be determined in a number of different ways, such as by taking the average of all four reflectance readings and assigning the average value to the decode reading. Alternatively, the reflectance reading that was taken from a central portion of the reagent pad 30, such as either one of the portions 64, 65 shown in FIG. 5, could be used as the decode reading.

At step 310, if the value of the decode reading is less than a threshold T1, such as 10.3% reflectance, the program branches to step 312 where the urine sample is categorized as having a relatively large blood concentration, which fact is stored in the RAM 204. At step 314, if the decode reading is less than a threshold T2, such as 19.7% reflectance, the program branches to step 316 where the urine sample is categorized as having a medium blood concentration. If the program reaches step 316, then the decode reading will have a value between the T2 and T3 thresholds (e.g. between 19.7% and 29.1% reflectance), in which case the program will branch to step 318 where the urine sample is categorized as having a relatively small blood concentration.

If not all four reflectance readings were less than the T3 threshold as determined at step 306, the program branches to step 320, where it determines whether at least three of the readings are greater than a threshold T4 (such as 56.0% reflectance), in which case the program branches to step 322 where the urine sample is categorized as being "negative" or having no blood present.

If the program reaches step 324 (in which case at least two of the reflectance readings were between the T3 and T4 thresholds as determined at steps 306, 320), then the urine sample is considered to have a trace amount of blood present. This trace amount of blood can be composed of either hemolyzed blood or non-hemolyzed blood.

Referring to FIG. 5, when non-hemolyzed blood cell fragments 67 come into contact with the reagent pad 30, they appear to be dark splotches, whereas the remaining portions of the reagent pad 30 appear to be light in color. Consequently, the four reflectance readings, each of which is taken from one of the illuminated portions 63–66, can vary substantially in value, depending upon whether the blood cell fragments 67 are present within the illuminated portion. For example, the illuminated portion 65 covers an area which completely encompasses one blood cell fragment 67 and parts of two others, whereas the illuminated portion 66 covers an area which encompasses no blood cell fragments 67. Consequently, the value of the reflectance reading associated with the illuminated portion 65 would be substantially different than the value of the reflectance reading associated with the illuminated portion 66.

Referring to FIG. 7, at step 324 the program determines the difference between the largest and smallest of the four reflectance reading values. At step 326, if that difference is greater than a predetermined value K (such as 2.5% reflectance), it is assumed that non-hemolyzed blood is present, and the program branches to step 328 where the urine sample is categorized as having a trace amount of non-hemolyzed blood.

If the difference between the largest and smallest reflectance readings is not greater than the value K as determined at step 326 (meaning that all four reflectance readings have substantially the same values), the program branches to step 330 where the urine sample is categorized as having a trace amount of blood.

At step 332, the category to which the urine sample was assigned (at one of steps 312, 316, 318, 322, 328 or 330) is output, such as by generating a printed record of the category and/or displaying the category on the visual display 16.

Modifications and alternative embodiments of the invention will be apparent to those skilled in the art in view of the foregoing description. This description is to be construed as illustrative only, and is for the purpose of teaching those skilled in the art the best mode of carrying out the invention.

The details of the structure and method may be varied substantially without departing from the spirit of the invention, and the exclusive use of all modifications which come within the scope of the appended claims is reserved.

What is claimed and sought to be secured by Letters Patent of the United States is:

1. An apparatus for analyzing a urine sample disposed on a reagent pad to detect non-hemolyzed levels of occult blood in said urine sample, said apparatus comprising:
   means for successively illuminating a plurality of different portions of said reagent pad on which said urine sample is disposed;
   means for detecting light received from said reagent pad, said detecting means generating a plurality of reflectance signals each having a magnitude, each of said reflectance signals being generated in response to light received from a corresponding one of said different portions of said reagent pad illuminated by said illuminating means;
   means for determining a difference between said magnitude of one of said reflectance signals and said magnitude of another of said reflectance signals; and
   means for comparing said difference with a predetermined threshold to detect the presence of non-hemolyzed blood in said urine sample.

2. An apparatus as defined in claim 1 wherein said means for determining said difference comprises:
   means for determining which of said reflectance signals has the largest magnitude;
   means for determining which of said reflectance signals has the smallest magnitude; and
   means for determining a difference between said largest magnitude and said smallest magnitude of said reflectance signals.

3. An apparatus as defined in claim 1 wherein said illuminating means comprises means for successively illuminating a plurality of overlapping portions of said reagent pad.

4. An apparatus as defined in claim 1 wherein said illuminating means comprises means for successively illuminating at least three different portions of said reagent pad which are linearly offset from each other.

5. An apparatus as defined in claim 1 wherein said illuminating means comprises:
   a light bulb (46); and
   means (220) for providing relative movement between said light bulb and said reagent pad (30).

6. An apparatus as defined in claim 5 additionally comprising a tray (20) in which said reagent pad (30) is disposed, wherein said light bulb (46) is disposed in a fixed position and wherein said means (220) for providing relative movement between said light bulb (46) and said reagent pad (30) comprises means for moving said tray.

7. An apparatus as defined in claim 1 additionally comprising means for determining whether said magnitudes of a plurality of said reflectance signals are within a predetermined range.

8. An apparatus as defined in claim 7 wherein said means for determining whether said magnitudes of a plurality of said reflectance signals are within a predetermined range comprises means for successively comparing said plurality of said reflectance signals to an upper threshold defining a first end of said range and a lower threshold defining a second end of said range.

9. An apparatus for analyzing a body-fluid sample disposed on a reagent pad, said apparatus comprising:
   means for successively illuminating a plurality of different portions of said reagent pad on which said body-fluid sample is disposed;
   means for detecting light received from said reagent pad, said detecting means generating a plurality of reflectance signals each having a magnitude, each of said reflectance signals being generated in response to light received from a corresponding one of said different portions of said reagent pad illuminated by said illuminating means; and
   means for determining whether said magnitude of one of said reflectance signals is substantially different than said magnitude of another of said reflectance signals.

10. An apparatus as defined in claim 9 additionally comprising:
    means for determining a decode signal based upon said reflectance signals; and
    means comparing said decode signal with a plurality of predetermined thresholds to categorize said body-fluid sample.

11. An apparatus as defined in claim 10 wherein said means for determining a decode signal comprises means for selecting one of said reflectance signals as said decode signal.

12. An apparatus as defined in claim 10 wherein said means for determining a decode signal comprises means for determining said decode signal based on an average of a plurality of said reflectance signals.

13. An apparatus as defined in claim 9 wherein said illuminating means comprises means for successively illuminating a plurality of overlapping portions of said reagent pad.

14. An apparatus as defined in claim 9 wherein said illuminating means comprises means for successively illuminating at least three different portions of said reagent pad which are linearly offset from each other.

15. A method of analyzing a urine sample disposed on a reagent pad, said method comprising the steps of:
    (a) illuminating a first portion of said reagent pad;
    (b) detecting light received from said first portion of said reagent pad;
    (c) generating a first reflectance signal having a magnitude based on said light detected during said step (b);
    (d) illuminating a second portion of said reagent pad, said second portion being different from said first portion;
    (e) detecting light received from said second portion of said reagent pad;
    (f) generating a second reflectance signal having a magnitude based on said light detected during said step (e); and
    (g) determining whether said magnitude of said first reflectance signal is substantially different than said magnitude of said second reflectance signal.

16. A method as defined in claim 15 wherein said step (g) comprises the steps of:
    (g1) determining a difference between said magnitude of said first reflectance signal and said magnitude of said second reflectance signal; and
    (g2) comparing said difference with a threshold to determine whether said difference is greater than said threshold.

17. A method as defined in claim 15 wherein said step (d) comprises the step of illuminating a portion of said reagent pad that overlaps said first portion of said reagent pad.

18. A method as defined in claim 15 wherein said step (g) comprises the steps of:

(h) determining a decode signal based upon said reflectance signals; and (i) comparing said decode signal with a plurality of predetermined thresholds to categorize said urine sample.

19. An apparatus for illuminating a body-fluid sample disposed on a reagent pad, said reagent pad having an overall area, said apparatus comprising:

means for illuminating a first portion of said reagent pad on which said body-fluid sample is disposed, said first portion of said reagent pad having an area that is smaller than said overall area of said reagent pad;

means for moving said reagent pad relative to said illuminating means so that said illuminating means illuminates a second portion of said reagent pad different from said first portion of said reagent pad, said second portion of said reagent pad having an area that is smaller than said overall area of said reagent pad; and means for detecting light received from said illuminated portions of said reagent pad.

20. An apparatus as defined in claim 19 wherein said illuminating means comprises a light bulb and a wall portion disposed between said light bulb and said reagent pad, said wall portion having an aperture positioned to be illuminated by said light bulb so that light which passes through said aperture illuminates said first and second portions of said reagent pad.

21. An apparatus as defined in claim 19 wherein said illuminating means comprises means for successively illuminating a plurality of overlapping portions of said reagent pad.

22. An apparatus as defined in claim 19 wherein said illuminating means comprises means for successively illuminating at least three different portions of said reagent pad which are linearly offset from each other.

* * * * *